United States Patent [19]

Ramachandran

[11] Patent Number: 4,785,131

[45] Date of Patent: * Nov. 15, 1988

[54] SUBSTITUTED CYANONAPHTHALENE PROCESS

[75] Inventor: Venkataraman Ramachandran, Baton Rouge, La.

[73] Assignee: Ethyl Corporation, Richmond, Va.

[*] Notice: The portion of the term of this patent subsequent to Aug. 9, 2005 has been disclaimed.

[21] Appl. No.: 112,399

[22] Filed: Oct. 26, 1987

[51] Int. Cl.[4] ............................................. C07C 120/00
[52] U.S. Cl. ..................................... 558/423; 558/426
[58] Field of Search ................. 558/423; 585/410, 411

[56] References Cited

U.S. PATENT DOCUMENTS 3,184,498  5/1965  Bolhofer ............................ 558/423
4,590,010  5/1986  Ramachandran et al. ......... 558/341

*Primary Examiner*—Joseph Paul Brust
*Attorney, Agent, or Firm*—Patricia J. Hogan

[57] ABSTRACT

6-Alkoxy-5-halo-1-cyanonaphthalenes, useful as pharmaceutical intermediates, are prepared by (1) reacting a 6-alkoxytetralone with cyanide ion and a Lewis acid in a nitroalkane or nitroarene solvent to form a 6-alkoxy-1-cyano-3,4-dihydronaphthalene, (2) intimately mixing the resultant solution with an aqueous base selected from alkali metal, alkaline earth metal, and tetraalkylammonium hydroxides, alkoxides, carbonates, and bicarbonates to aromatize the 6-alkoxy-1-cyano-3,4-dihydronaphthalene, and (3) halogenating the resultant 6-alkoxy-1-cyanonaphthalene while still in the nitroalkane or nitroarene solvent.

18 Claims, No Drawings

SUBSTITUTED CYANONAPHTHALENE PROCESS

FIELD OF THE INVENTION

This invention relates to 6-alkoxy-5-halo-1-cyanonaphthalene and more particularly to processes for preparing them.

BACKGROUND

As disclosed in U.S. Pat. No. 4,590,010 (Ramachandran et al. I), it is known that 6-alkoxy-5-halo-1-cyanonaphthalenes are useful as pharmaceutical intermediates and that they can be prepared by (1) reacting a 6-alkoxytetralone with cyanide ion and a Lewis acid in a suitable solvent, such as nitrobenzene, to cyanate it to a 6-alkoxy-1-cyano-3,4-dihydronaphthalene, (2) aromatizing the resultant 6-alkoxy-1-cyano-3,4-dihydronaphthalene, preferably by dehydrogenation in the presence of a palladium-on-carbon catalyst, (3) isolating the resultant 6-alkoxy-1-cyanonaphthalene, and (4) halogenating it in a suitable solvent, such as a halogenated alkane. This process, although generally satisfactory, is somewhat inconvenient because of the number of steps required to isolate the 6-alkoxy-1-cyanonaphthalene for halogenation.

Copending application Ser. No. 880,070 (Ramachandran et al. II), filed June 30, 1986, teaches that a 6-alkoxy-1-cyano-3,4-dihydronaphthalene can be aromatized by intimately mixing it with a base selected from alkali metal, alkaline earth metal, and tetraalkylammonium hydroxides, alkoxides, carbonates, and bicarbonates in the presence of a hydrogen acceptor, such as nitrobenzene. The use of nitrobenzene in the reaction has the disadvantage of leading to the formation of azoxybenzene, a compound which is difficult to separate from the 6-alkoxy-1-cyanonaphthalene.

SUMMARY OF THE INVENTION

An object of the invention is to provide a novel process for preparing 6-alkoxy-5-halo-1-cyanonaphthalenes.

Another object is to provide such a process which minimizes the distillation and solids handling steps required.

A further object is to provide such a process which includes a base aromatization in a nitro solvent but permits easy removal of the azoxy compound formed in the process.

These and other objects are attained by (1) cyanating a 6-alkoxytetralone by reacting it with cyanide ion and a Lewis acid in a nitroalkane or nitroarene solvent so as to form a 6-alkoxy-1-cyano-3,4-dihydronaphthalene, (2) intimately mixing the resultant solution with an aqueous base selected from alkali metal, alkaline earth metal, and tetraalkylammonium hydroxides, alkoxides, carbonates, and bicarbonates so as to aromatize the 6-alkoxy-1-cyano-3,4-dihydronaphthalene, and (3) halogenating the resultant 6-alkoxy-1-cyanonaphthalene while still in the nitroalkane or nitroarene solvent so as to form a 6-alkoxy-5-halo-1-cyanonaphthalene.

DETAILED DESCRIPTION

As in Ramachandran et al. I, the teachings of which are incorporated herein in toto by reference, the 6-alkoxytetralone used in the process may be any 6-alkoxytetralone capable of being converted to a 6-alkoxy-5-halo-1-cyanonaphthalene thereby, including the 6-alkoxytetralones wherein the 6-substituent is an alkoxy group containing 1-20 carbons. However, the preferred 6-alkoxytetralones are those wherein the 6-substituent is an alkoxy group containing 1-6 carbons, most preferably a straight-chain alkoxy group of 1-3 carbons or a branched-chain alkoxy group of three or four carbons, such as methoxy, ethoxy, 1-methylethoxy, butoxy, hexoxy, etc. A particularly preferred 6-alkoxytetralone is 6-methoxytetralone.

The cyanide ion with which the 6-alkoxytetralone is reacted may be provided by any known sources of cyanide ion that is free of radicals which would stabilize the cyanohydrin that is believed to be initially formed in the reaction. However, it is most commonly provided by hydrogen cyanide, a tri- or tetraalkylammonium cyanide (generally such a compound containing up to about 50 carbons) such as trimethylammonium cyanide, tributylmethylammonium cyanide, tetrabutylammonium cyanide, etc., or a metal cyanide, such as cuprous cyanide or an alkali or alkaline earth metal cyanide such as lithium, sodium, potassium, rubidium, cesium, beryllium, magnesium, calcium, strontium, or barium cyanide. The sodium, potassium, and hydrogen cyanides are generally the preferred sources of cyanide ion. The amount of cyanide ion employed is not critical, but it is usually desirable to employ about 1-5, preferably about 1-2, mols of cyanide ion per mol of 6-alkoxytetralone to produce good yields of product.

The Lewis acid employed in the cyanation step may be hydrogen fluoride, a trialkylaluminum, or the like but is preferably a metal halide, such as boron or aluminum trifluoride, triiodide, trichloride, or tribromide, tin tetrachloride, zinc dichloride, gallium trichloride, titanium tetrachloride, diethylaluminum chloride, ethylaluminum dichloride, ethoxyaluminum dichloride, diethoxyaluminum chloride, hydroxyaluminum dichloride, dihydroxyaluminum chloride, and other such compounds wherein at least one halogen is attached to a metal atom, any remaining valences of which are usually satisfied by hydroxy, hydrocarbyl, or hydrocarbyloxy groups, generally hydroxy or alkyl or alkoxy groups containing 1-10 carbons. The preferred Lewis acids are boron trifluoride and aluminum chloride, especially aluminum chloride. This ingredient of the reaction mixture is ordinarily employed in the amount of about 0.5-1.5, preferably about 1-1.1, mols per mol of the 6-alkoxytetralone, although smaller or larger amounts can be used if desired.

As mentioned above, the solvent employed in the cyanation and subsequent steps of the process is a nitroalkane or nitroarene, e.g., nitroethane, 1-nitrohexane, 3-nitro-2,2-dimethylbutane, 2-nitro-2-methylpentane, nitrobenzene, 2-, 3-, and 4-nitrotoluenes, 2- and 4-nitroethylbenzenes, 2-nitro-1,3,5-trimethylbenzene, nitronaphthalenes, etc. The nitroarenes, especially nitrobenzene, are preferred.

In the practice of the cyanation reaction, the ingredients of the reaction mixture may be combined in any suitable manner, preferably with the solids in finely-divided form, and heated at a suitable temperature, e.g., about 60°-120° C., preferably about 90° C., to produce the desired 6-alkoxy-1-cyano-3,4-dihydronaphthalene. Lower temperatures can be used but are less desirable because of their leading to slower reactions; higher temperatures are apt to be undesirable because of the tendency for by-products to be formed at the higher temperatures. The time required to obtain good yields varies with the temperature but is frequently in the range of about 4-10 hours.

It is sometimes preferred to combine the ingredients by prestirring the cyanide ion source, the Lewis acid, and the solvent before combining these ingredients with the 6-alkoxytetralone, and it appears to be desirable to maintain the temperature of these ingredients below 60° C., e.g., at about 10°-50° C., conveniently at about 20°-30° C., until the addition of the 6-alkoxytetralone has been completed.

It is also sometimes preferred, especially when the cyanide ion source is an alkali metal cyanide, to conduct the cyanation in the presence of a small amount of water and/or concentrated HCl—additives which appear to effect an activation of one or more of the reactants and increase yields. The particular amount of water and/or HCl employed is an activating amount, i.e., an amount insufficient to hydrolyze the Lewis acid completely, and may be provided simply by the water naturally present in one or more of the aforementioned ingredients of the reaction mixture. When it is desired to employ additional water and/or HCl, the added amount is generally in the range of about 0.1-1.0 mol per mol of the 6-alkoxytetralone.

It is frequently preferred to conduct either or both of the cyanation and subsequent aromatization steps in the presence of a phase transfer agent, e.g. a crown ether such as 12-crown-4, 15-crown-5, 18-crown-6, etc.; an alcohol such as methanol, ethanol, etc.; a polyalkylene glycol such as PEG 600, etc.; an alkylammonium or alkylphosphonium salt, etc. The phase transfer agents most commonly used are the alkylammonium and alkylphosphonium salts, especially the bromides or other halides, such as tetramethyl, tetraethyl, tetrapropyl, tetrabutyl, tetrapentyl, tetrahexyl, tetraheptyl, methyltributyl, methyltrioctyl, methyltrialkyl($C_8$–$C_{10}$), butyltripropyl, heptyltriethyl, octyltriethyl, dodecyltrimethyl, dodecyltriethyl, tetradecyltrimethyl, and hexadecyltrimethylammonium bromides, chlorides, iodides, and fluorides; trimethyl, triethyl, methyldiisopropyl, and ethyldiisopropylammonium hydrogen halides; the corresponding alkylphosphonium halides, etc. The preferred phase transfer agents are tetraalkylammonium halides wherein the alkyl groups contain 1-20, most commonly 1-12, carbons. When employed, the phase transfer agent is usually used in a concentration of about 0.001-10 mol percent, based on the amount of 6-alkoxytetralone employed.

When the cyanation has been completed, the resultant solution is intimately mixed with an aqueous base to aromatize the 6-alkoxy-1-cyano-3,4-dihydronaphthalene. The base employed as an aromatizing agent may be an alkali metal, alkaline earth metal, or tetraalkylammonium hydroxide, alkoxide, carbonate, or bicarbonate. When the cation is a metal atom, it may be lithium, sodium, potassium, rubidium, cesium, calcium, strontium, or barium. When it is a tetraalkylammonium group, it may be any such group in which the alkyl groups are the same or different, straight-chain or branched, and contain about 1-20 carbons, usually about 1-12 carbons, such as tetramethyl, tetraethyl, tetrapropyl, tetrabutyl, tetrapentyl, tetrahexyl, tetraheptyl, methyltributyl, methyltrioctyl, methyltrialkyl($C_8$–$C_{10}$), butyltripropyl, heptyltriethyl, octyltriethyl, dodecyltrimethyl, dodecyltriethyl, tetradecyltrimethyl, and hexadecyltrimethylammonium groups, etc. Any alkoxide of such cations may be used, but those containing 1-4 carbons, e.g., methoxides, ethoxides, isopropoxides, and t-butoxides, are apt to be preferred over higher alkoxides because of availability. Also, as already indicated, the base may be a carbonate or bicarbonate. The hydroxides, however, are preferred, and the most preferred bases are the alkali metal hydroxides, especially sodium or potassium hydroxide.

Although smaller amounts are frequently operable, the amount of base used is generally at least about 0.05 mol, most commonly at least about 0.1 mol, per mol of the 6-alkoxy-1-cyano-3,4-dihydronaphthalene. There is no maximum to the amount that may be employed, and it is preferred to use at least enough base to serve both as an aromatizing agent and a wash for removing inorganic residues from the cyanation step.

In the conduct of the aromatization, intimate contact of the ingredients of the reaction mixture is maintained by stirring. It may be necessary to heat the mixture initially to start the reaction when the ingredients have been contacted at a temperature below 15° C. but, once started, the reaction is exothermic and normally does not require additional external heating. However, when the reaction appears sluggish, external heat can be applied to provide reaction temperatures up to about 100° C.

After completion of the aromatization, the reaction mixture is allowed to separate into a base phase and a nitroalkane or nitroarene phase, and the latter phase is treated to halogenate the 6-alkoxy-1-cyanonaphthalene. The halogenation may be a fluorination, chlorination, bromination, or iodination and may be accomplished by known techniques, such as the techniques disclosed in March, *Advanced Organic Chemistry*, Second Edition, McGraw-Hill, New York, pp. 482-484, the teachings of which are incorporated herein by reference. However, in a preferred embodiment of the invention, the halogenation is a bromination. The bromination is accomplished so easily that it is not even necessary to employ a catalyst, though conventional bromination catalysts can be utilized without adversely affecting the reaction. Thus, it is ordinarily preferred to halogenate the 6-alkoxy-1-cyanonaphthalene simply by reacting it with bromine in the nitroalkane or nitroarene solvent at any suitable temperature, e.g., about −5° C. to about 30° C., conveniently at room temperature. Lower reaction temperatures can be used but do not appear to offer any particular advantage, and higher temperatures are also utilizable but are conducive to the loss of bromine.

The reaction results in the formation of a 6-alkoxy-5-halo-1-cyanonaphthalene which, being insoluble in the nitroalkane or nitroarene solvent, is easily separated from the soluble azoxy derivative of the solvent—a derivative which is inherently formed in the aromatization step. As indicated above, the process is advantageous in its minimizing the distillation and solids handling steps required for the preparation of 6-alkoxy-5-halo-1-cyanonaphthalenes, compounds which are useful as pharmaceutical intermediates.

The following example is given to illustrate the invention and is not intended as a limitation thereof.

EXAMPLE

A mixture of 25.25 g of dry aluminum chloride, 16.7 g of sodium cyanide, 1.7 g of tetrabutylammonium bromide, and 20 drops of concentrated HCl in 170 mL of nitrobenzene was stirred for two hours under a nitrogen atmosphere. Then 30 g of 6-methoxytetralone was added, and the reaction mixture was stirred at 90° C. for six hours to form 6-methoxy-1-cyano-3,4-dihydronaphthalene. A 200-mL portion of 20% NaOH was added, and the reaction mixture became warm and was stirred vigorously at 60° C. for one hour. The phases were allowed to separate. After the nitrobenzene phase had been transferred to another vessel, 35 g of bromine was slowly added and a precipitate formed. The reaction mixture was then heated to remove any HBr, cooled, and worked up to provide 28 g of 6-methoxy-5-bromo-1-cyanonaphthalene.

It is obvious that many variations can be made in the products and processes set forth above without departing from the spirit and scope of this invention.

What is claimed is:

1. A process which comprises (1) cyanating a 6-alkoxy-tetralone which has 1–20 carbons in the alkoxy group by reacting it with hydrogen cyanide, a tri- or tetraalkylammonium cyanide, or a metal cyanide and a Lewis acid in a nitroalkane or nitroarene solvent at about 60°–120° C. so as to form a 6-alkoxy-1-cyano-3,4-dihydronaphthalene, (2) intimately mixing the resultant solution with an aqueous base selected from alkali metal and tetralkylammonium hydroxides and alkoxides at about 15°–100° C. so as to aromatize the 6-alkoxy-1-cyano-3,4-dihydronaphthalene, and (3) halogenating the resultant 6-alkoxy-1-cyanonaphthalene while still in the nitroalkane or nitroarene solvent so as to form a 6-alkoxy-5-halo-1-cyanonaphthalene.

2. The process of claim 1 wherein the 6-alkoxytetralone is 6-methoxytetralone.

3. The process of claim 1 wherein the cyanide ion is hydrogen cyanide.

4. The process of claim 1 wherein the cyanide ion is an alkali metal cyanide.

5. The process of claim 4 wherein the alkali metal cyanide is sodium cyanide.

6. The process of claim 1 wherein the Lewis acid is aluminum chloride.

7. The process of claim 1 wherein the solvent is a nitroarene.

8. The process of claim 7 wherein the nitroarene is nitrobenzene.

9. The process of claim 1 wherein the base is a hydroxide.

10. The process of claim 9 wherein the base is an alkali metal hydroxide.

11. The process of claim 10 wherein the base is sodium hydroxide.

12. The process of claim 10 wherein the base is potassium hydroxide.

13. The process of claim 1 wherein the cyanation is conducted in the presence of an activating amount of water and/or concentrated HCl.

14. The process of claim 1 wherein the cyanation and aromatization are conducted in the presence of a phase transfer agent.

15. The process of claim 14 wherein the phase transfer agent is a tetraalkylammonium halide in which the alkyl groups contain 1–20 carbons.

16. The process of claim 1 wherein the 6-alkoxy-1-cyanonaphthalene is halogenated by reacting it with bromine.

17. A process which comprises (1) cyanating 6-methoxy-tetralone by reacting it with hydrogen cyanide and aluminum chloride in nitrobenzene at about 60°–120° C. so as to form 6-methoxy-1-cyano-3,4-dihydronaphthalene, (2) intimately mixing the resultant solution with an aqueous solution of sodium hydroxide or potassium hydroxide in the presence of a phase transfer agent at about 15°–100° C. as as to aromatize the 6-methoxy-1-cyano-3,4-dihydronaphthalene, and (3) brominating the resultant 6-methoxy-1-cyanonaphthalene while still in nitrobenzene so as to form 6-methoxy-5-bromo-1-cyanonaphthalene.

18. A process which comprises (1) cyanating 6-methoxy-tetralone by reacting it with sodium cyanide and aluminum chloride in the presence of a phase transfer agent, an activating amount of water and/or concentrated HCl, and nitrobenzene at about 60°–120° C. so as to form 6-methoxy-1-cyano-3,4-dihydronaphthalene, (2) intimately mixing the resultant solution with an aqueous solution of sodium hydroxide or potassium hydroxide at about 15°–100° C. so as to aromatize the 6-methoxy-1-cyano-3,4-dihydronaphthalene, and (3) brominating the resultant 6-methoxy-1-cyanonaphthalene while still in nitrobenzene so as to form 6-methoxy-5-bromo-1-cyanonaphthalene.

* * * * *